(12) United States Patent
Muramatsu et al.

(10) Patent No.: US 8,802,402 B2
(45) Date of Patent: Aug. 12, 2014

(54) MUTANT POLYHYDROXYALKANOIC ACID SYNTHASE GENE AND METHOD FOR PRODUCING ALIPHATIC POLYESTER USING THE SAME

(75) Inventors: Masayoshi Muramatsu, Nishikamo-gun (JP); Hiromi Kambe, Seto (JP); Masakazu Ito, Toyota (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 13/809,536

(22) PCT Filed: Jul. 14, 2010

(86) PCT No.: PCT/JP2010/061871
§ 371 (c)(1),
(2), (4) Date: Jan. 10, 2013

(87) PCT Pub. No.: WO2012/008023
PCT Pub. Date: Jan. 19, 2012

(65) Prior Publication Data
US 2013/0157327 A1 Jun. 20, 2013

(51) Int. Cl.
*C12P 7/62* (2006.01)

(52) U.S. Cl.
CPC ..................... *C12P 7/625* (2013.01)
USPC ..... 435/135; 435/132; 435/320.1; 435/252.3; 435/252.31; 435/252.32; 435/252.33; 435/252.34; 435/254.11; 435/254.2; 435/254.21; 435/254.22; 536/23.1

(58) Field of Classification Search
None
See application file for complete search history.

(56) References Cited

U.S. PATENT DOCUMENTS

| 4,477,654 | A | 10/1984 | Holmes et al. | |
| 2009/0226988 | A1* | 9/2009 | Tajima et al. | 435/135 |
| 2010/0050298 | A1 | 2/2010 | Park et al. | |
| 2010/0136637 | A1 | 6/2010 | Park et al. | |
| 2011/0104768 | A1* | 5/2011 | Taguchi et al. | 435/135 |
| 2011/0183388 | A1* | 7/2011 | Sabirova et al. | 435/135 |
| 2011/0212497 | A1* | 9/2011 | Obata et al. | 435/135 |
| 2012/0122165 | A1* | 5/2012 | Obata et al. | 435/135 |
| 2013/0045516 | A1* | 2/2013 | Muramatsu et al. | 435/135 |
| 2013/0157327 | A1* | 6/2013 | Muramatsu et al. | 435/135 |
| 2013/0164800 | A1* | 6/2013 | Ivanov et al. | 435/135 |

FOREIGN PATENT DOCUMENTS

| EP | 1 885 857 | 2/2008 |
| EP | 1 885 857 A | 2/2008 |
| JP | 57-150393 A | 9/1982 |

(Continued)

OTHER PUBLICATIONS

GenBank Accession No. YP 003731457.1; GI: 299769431; published Jun. 10, 2013.*
Jung et al., "Complete genome sequence of the diesel-degrading *Acinetobacter* sp. strain DR1", Journal of Bacteriology, vol. 192, No. 18, pp. 4794-4795, published online Jul. 16, 2010.*
Kalscheuer et al., "Analysis of storage lipid accumulation in Alcanivorax borkumensis: Evidence for alternative triacylglycerol biosynthesis routes in bacteria", Journal of Bacteriology, vol. 189, No. 3, pp. 918-928, 2007.*

(Continued)

*Primary Examiner* — Rebecca Prouty
*Assistant Examiner* — Richard Ekstrom
(74) *Attorney, Agent, or Firm* — Sughrue Mion, PLLC

(57) ABSTRACT

A substitution mutation that improves polymerization activity of a polyhydroxyalkanoic acid synthase is identified. At least 1 amino acid residue selected from the group consisting of a histidine residue at position 17, a proline residue at position 71, a valine residue at position 131, a methionine residue at position 205, a leucine residue at position 230, and a proline residue at position 239 of a polyhydroxyalkanoic acid synthase derived from *Alcanivorax borkumensis* is subjected to substitution mutation with another amino acid.

15 Claims, 3 Drawing Sheets

(56) References Cited

FOREIGN PATENT DOCUMENTS

| | | |
|---|---|---|
| JP | 2009-138174 A | 6/2009 |
| WO | 2006/126796 A1 | 11/2006 |
| WO | 2008/062999 A1 | 5/2008 |
| WO | 2009/091141 A2 | 7/2009 |
| WO | 2009/131186 A1 | 10/2009 |
| WO | 2010/050470 A1 | 6/2010 |
| WO | WO 2013153180 A1 * | 10/2013 |

OTHER PUBLICATIONS

Schneiker et al., "Genome sequence of the ubiquitous hydrocarbon-degrading marine bacterium Alcanivorax borkumensis", Nature Biotechnology, vol. 24, No. 8, pp. 997-1004, 2006.*
Database DDBJ/EMBL/GenBank [online], Accession No. Q0VPN2, Nov. 28, 2006 uploaded, Definition: Polyhydroxyalkanoate synthase [retrieved on Jul. 28, 2010] Retrieved from the Internet <URL:http://www.ncbi.nlm.nih.gov/protein/123345516>.

* cited by examiner

MUTANT POLYHYDROXYALKANOIC ACID SYNTHASE GENE AND METHOD FOR PRODUCING ALIPHATIC POLYESTER USING THE SAME

CROSS REFERENCE TO RELATED APPLICATIONS

This application is a National Stage of International Application No. PCT/JP2010/061871 filed Jul. 14, 2010, the contents of which are incorporated herein by reference in their entirety.

TECHNICAL FIELD

The present invention relates to a mutant polyhydroxyalkanoic acid synthase gene comprising at least one substitution mutation, a recombinant microorganism into which such gene has been introduced, and a method for producing aliphatic polyester using the same.

BACKGROUND ART

Aliphatic polyesters have drawn attention as biodegradable plastics, which can be easily degraded in nature, and as "green" plastics, which can be synthesized from renewable carbon resources such as sugar or vegetable oil. At present, for example, a polylactic acid having a polylactic acid backbone has been put to practical use as an aliphatic polyester.

An example of a known technique for producing an aliphatic polyester such as polylactic acid with the use of recombinant microorganisms is disclosed in Patent Document 1 (WO 2006/126796). Patent Document 1 discloses a recombinant *E. coli* cell resulting from introduction of a gene encoding an enzyme converting a lactic acid into lactyl-CoA and a gene encoding an enzyme synthesizing polyhydroxyalkanoic acid using lactyl-CoA as a substrate into a host *E. coli* cell. The technique disclosed by Patent Document 1 involves the use of the pct gene derived from *Clostridium propionicum* as a gene encoding an enzyme converting a lactic acid into lactyl-CoA. In this technique, the phaC2 gene derived from the *Pseudomonas* sp. 61-3 strain is used as a gene encoding an enzyme synthesizing polyhydroxyalkanoic acid using lactyl-CoA as a substrate.

However, the technique of Patent Document 1 is insufficient in terms of the productivity of aliphatic polyesters, such as polylactic acids, and various attempts made aimed at improving such productivity have been insufficient. For example, Patent Document 2 (WO 2008/062999) discloses an attempt to enhance the capacity to synthesize a lactic acid homopolymer or polylactic acid copolymer using lactide-CoA as a substrate via introduction of a given mutation into the phaC1 gene derived from the *Pseudomonas* sp. 6-19 strain. In addition, Patent Document 3 (WO 2009/131186) discloses a technique for producing a polymer comprising 3-hydroxybutyric acid and lactic acid by introducing a given mutation into the phaC1 gene derived from the *Pseudomonas* sp. 61-3 strain to cause mutations in amino acids at positions 130, 325, 477, and 481.

PRIOR ART DOCUMENTS

Patent Document 1 WO 2006/126796
Patent Document 2 WO 2008/062999
Patent Document 3 WO 2009/131186

SUMMARY OF THE INVENTION

Object to be Attained by the Invention

While conventional techniques described above are capable of providing recombinant microorganisms having the capacity to synthesize aliphatic polyesters such as polylactic acids, such techniques are disadvantageous because of its low productivity of aliphatic polyesters, and such techniques cannot be regarded as being thoroughly examined from the viewpoint of improvement in productivity. Accordingly, the present invention is intended to provide a mutant polyhydroxyalkanoic acid synthase gene having excellent polymerization activity, a recombinant microorganism into which such gene has been introduced, and a method for producing an aliphatic polyester using the same.

Means for Attaining the Object

The present inventors have conducted concentrated studies in order to attain the above object. As a result, they succeeded in obtaining a polyhydroxyalkanoic acid synthase exhibiting significant improvement in the polymerization activity via introduction of a given mutation into the polyhydroxyalkanoic acid synthase gene derived from a given microorganism, thereby completing the present invention.

Specifically, the present invention includes the following.

(1) A gene encoding a mutant hydroxyalkanoic acid synthase resulting from substitution mutation of at least 1 amino acid residue selected from the group consisting of a histidine residue at position 17, a proline residue at position 71, a valine residue at position 131, a methionine residue at position 205, a leucine residue at position 230, and a proline residue at position 239 of the polyhydroxyalkanoic acid synthase derived from *Alcanivorax borkumensis* comprising the amino acid sequence as shown in SEQ ID NO: 2 with another amino acid.

(2) The gene encoding the mutant hydroxyalkanoic acid synthase according to (1), wherein the histidine residue at position 17 is substituted with an amino acid selected from the group consisting of leucine, valine, isoleucine, and methionine, the proline residue at position 71 is substituted with serine or threonine, the valine residue at position 131 is substituted with isoleucine, the methionine residue at position 205 is substituted with threonine or serine, the leucine residue at position 230 is substituted with methionine, and the proline residue at position 239 is substituted with an amino acid selected from the group consisting of leucine, valine, isoleucine, and methionine.

(3) The gene encoding the mutant hydroxyalkanoic acid synthase according to (1), wherein the histidine residue at position 17 is substituted with leucine, the proline residue at position 71 is substituted with serine, the valine residue at position 131 is substituted with isoleucine, the methionine residue at position 205 is substituted with threonine, the leucine residue at position 230 is substituted with methionine, and the proline residue at position 239 is substituted with leucine.

(4) The gene encoding the mutant hydroxyalkanoic acid synthase according to (1), which has a single substitution mutation of the proline residue at position 239.

(5) The gene encoding the mutant hydroxyalkanoic acid synthase according to (4), wherein an amino acid is substituted with leucine.

(6) The gene encoding the mutant hydroxyalkanoic acid synthase according to (1), which has a single substitution mutation of the valine residue at position 131.

(7) The gene encoding the mutant hydroxyalkanoic acid synthase according to (6), wherein an amino acid is substituted with isoleucine.

(8) The gene encoding the mutant hydroxyalkanoic acid synthase according to (1), which has substitution mutations of the histidine residue at position 17, the proline residue at position 71, and the methionine residue at position 205.

(9) The gene encoding the mutant hydroxyalkanoic acid synthase according to (8), wherein the histidine residue at position 17 is substituted with leucine, the proline residue at position 71 is substituted with serine, and the methionine residue at position 205 is substituted with threonine.

(10) The gene encoding the mutant hydroxyalkanoic acid synthase according to (1), which has a single substitution mutation of the leucine residue at position 230.

(11) The gene encoding the mutant hydroxyalkanoic acid synthase according to (10), wherein an amino acid is substituted with methionine.

(12) A mutant hydroxyalkanoic acid synthase encoded by the gene according to any of (1) to (11).

(13) An expression vector comprising the gene according to any of (1) to (11).

(14) The expression vector according to (13), which further comprises a gene encoding an enzyme that converts hydroxyalkanoic acid into hydroxyalkanoic acid CoA.

(15) The expression vector according to (14), wherein the gene encoding an enzyme is the propionyl CoA transferase gene derived from *Megasphaera elsdenii* or *Staphylococcus aureus*.

(16) A recombinant microorganism into which the gene according to any of (1) to (11) and a gene encoding an enzyme that converts hydroxyalkanoic acid into hydroxyalkanoic acid CoA have been introduced.

(17) The recombinant microorganism according to (16), wherein the gene encoding an enzyme is the propionyl CoA transferase gene derived from *Megasphaera elsdenii* or *Staphylococcus aureus*.

(18) The recombinant microorganism according to (17), wherein a host microorganism is *E. coli*.

(19) A method for producing aliphatic polyester comprising culturing the recombinant microorganism according to any of (16) to (18) in a medium and recovering aliphatic polyester.

(20) The method for producing aliphatic polyester according to (19), wherein the aliphatic polyester to be recovered is aliphatic polyester having the polylactic acid backbone.

(21) The method for producing aliphatic polyester according to (19), wherein the aliphatic polyester to be recovered is polylactic acid.

(22) The method for producing aliphatic polyester according to (19), wherein lactic acid is not added to a medium when culturing the recombinant microorganism.

Effects of the Invention

The present invention can provide a gene encoding a polyhydroxyalkanoic acid synthase having excellent polymerization activity. The productivity of aliphatic polyesters can be significantly improved with the use of the mutant hydroxyalkanoic acid synthase gene according to the present invention. In addition, a recombinant microorganism that is excellent in the productivity of aliphatic polyesters can be provided with the use of the mutant hydroxyalkanoic acid synthase gene according to the present invention. That is, the recombinant microorganism according to the present invention has a capacity for producing aliphatic polyesters that is significantly superior to that of existing recombinant microorganisms. With the use of the recombinant microorganism according to the present invention, further, a method for producing aliphatic polyesters that is excellent in terms of productivity can be provided.

EMBODIMENTS FOR CARRYING OUT THE INVENTION

Figure 1:
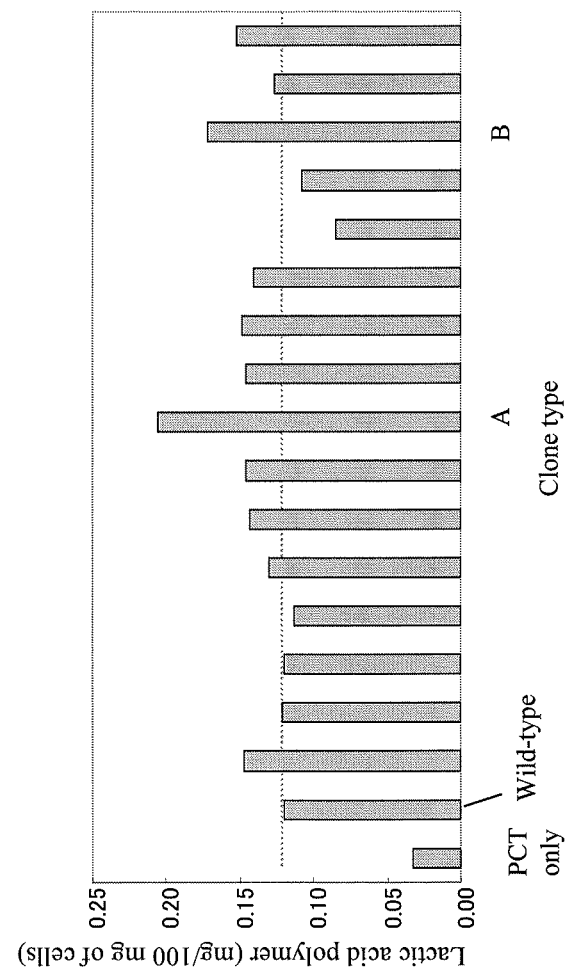
FIG. 1 is a characteristic diagram showing the amount of polylactic acids produced with the use of the transformed *E. coli* cells prepared in the examples.

Hereafter, the mutant hydroxyalkanoic acid synthase gene according to the present invention, the recombinant microorganism according to the present invention, and the method for producing aliphatic polyester using the same are described in detail.

The mutant hydroxyalkanoic acid synthase gene according to the present invention encodes a mutant polyhydroxyalkanoic acid synthase having substitution mutation of at least one given amino acid residue. Also, the recombinant microorganism according to the present invention results from introduction of such mutant polyhydroxyalkanoic acid synthase gene and the propionyl CoA transferase gene (the pct gene) into a host microorganism.

Mutant Polyhydroxyalkanoic Acid Synthase Gene

The mutant polyhydroxyalkanoic acid synthase gene encodes a mutant hydroxyalkanoic acid synthase resulting from the introduction of a given substitution mutation into a polyhydroxyalkanoic acid synthase derived from *Alcanivorax borkumensis*. An example of a gene derived from *Alcanivorax borkumensis* is a wild-type polyhydroxyalkanoic acid synthase gene (the phaC gene) endogenous in the *Alcanivorax borkumensis* SK2 strain. Specifically, the mutant hydroxyalkanoic acid synthase gene can be obtained by introducing a given substitution mutation into the phaC gene derived from the *Alcanivorax borkumensis* SK2 strain.

Specifically, substitution mutation in the mutant hydroxyalkanoic acid synthase can be defined based on the amino acid sequence of a wild-type hydroxyalkanoic acid synthase. The nucleotide sequence of a coding region of the phaC gene derived from the *Alcanivorax borkumensis* SK2 strain and the amino acid sequence of the wild-type hydroxyalkanoic acid synthase encoded by such gene are shown in SEQ ID NOs: 1 and 2. A protein comprising the amino acid sequence as shown in SEQ ID NO: 2 has activity of polyhydroxyalkanoic acid synthesis (and activity of synthesizing polylactic acid using lactyl-CoA as a substrate, in particular) or activity of synthesizing a polylactic acid-based copolymer using lactyl-CoA and another hydroxyalkanoic acid as substrates.

Substitution mutations in the mutant hydroxyalkanoic acid synthase are a histidine residue at position 17, a proline residue at position 71, a valine residue at position 131, a methionine residue at position 205, a leucine residue at position 230, and a proline residue at position 239 in the amino acid sequence as shown in SEQ ID NO: 2. The mutant hydroxyalkanoic acid synthase may have at least 1 substitution mutation or a plurality of substitution mutations selected from among these seven substitution mutations.

The term "substitution mutation" refers to conversion of a given amino acid of a wild-type protein into another amino acid. In the mutant hydroxyalkanoic acid synthase, specifically, it is sufficient if at least 1 amino acid residue selected from among a histidine residue at position 17, a proline residue at position 71, a valine residue at position 131, a methionine residue at position 205, a leucine residue at position 230, and a proline residue at position 239 is converted into another amino acid.

An amino acid may be substituted with any amino acid without particular limitation. Since polymerization activity inherent to the hydroxyalkanoic acid synthase is significantly enhanced, a given amino acid or a group of amino acids is preferable. More specifically, the histidine residue at position 17 is substituted with preferably an amino acid selected from the group consisting of leucine, valine, isoleucine, and methionine, with leucine being particularly preferable. Also, the proline residue at position 71 is substituted with preferably serine or threonine, with serine being more preferable. Further, the valine residue at position 131 is substituted with preferably isoleucine. Furthermore, the methionine residue at position 205 is substituted with preferably threonine or serine, with threonine being particularly preferable. Further, the leucine residue at position 230 is substituted with preferably methionine. The proline residue at position 239 is substituted with further preferably an amino acid selected from the group consisting of leucine, valine, isoleucine, and methionine, with leucine being particularly preferable.

Variations in amino acid residues can occur at given sites for the following reasons. As described in Reference (1): McKee & McKee Biochemistry, Third Edition, Chapter Five: Amino Acids, Peptides, and Proteins, 5.1: Amino Acids, Editor: Atsushi Ichikawa, Translator: Shinichi Fukuoka, Publisher: Ryosuke Sone, Publishing company: Kagaku-Dojin Publishing Company, Inc., ISBN4-7598-0944-9, it is well-known that amino acids are classified in accordance with side chains having similar properties (i.e., chemical properties or physical sizes). It is also well-known that substitution in molecular evolution frequently takes place between amino acid residues classified as members of a given group while maintaining protein activity. Based thereon, BLOSUM scoring matrices for substitution mutation of amino acid residues are proposed in FIG. 2 of Reference (2): Henikoff, S., Henikoff, J. G, Amino-acid substitution matrices from protein blocks, Proc. Natl. Acad. Sci., U.S.A., 89, 10915-10919, 1992, and such techniques are extensively employed. According to Reference (1), substitution of amino acids having similar side chain chemical properties leads to smaller changes in structures or functions that would influence the entire protein. According to References (1) and (2), amino acids that can undergo substitution mutation at the sites mentioned above can be determined based on indicators such as chemical properties or physical size. Such amino acids are indicated by the BLOSUM scoring matrices disclosed in Reference (2) as a group of amino acids having a score 0 or greater, and preferably a group of amino acids having a score 1 or greater. Examples of representative groups include the 8 groups described below. Amino acids may further be classified as a group of amino acids having the score 0 or greater, preferably a group of amino acids having the score 1 or greater, and more preferably a group of amino acids having the score 2 or greater.

1) Group of Aliphatic Hydrophobic Amino Acids (the ILMV Group)

Among the neutral non-polar amino acids indicated in Reference (1), amino acids classified as members of this group have aliphatic hydrophobic side chains, and this group includes V (Val, valine), L (Leu, leucine), I (Ile, isoleucine), and M (Met, methionine). Among amino acids that are classified as neutral non-polar amino acids according to Reference (1), FGACWP is not included in "the group of aliphatic hydrophobic amino acids" for the following reasons. That is, G (Gly, glycine) and A (Al, alanine) are smaller than a methyl group, and non-polar effects are weak. C (Cys, cysteine) occasionally plays a key role in an S—S bond, and it forms a hydrogen bond with an oxygen or nitrogen atom. F (Phe, phenylalanine) and W (Trp, tryptophan) have side chains with very large molecular weights, and aromatic compound effects are strong. P (Pro, proline) has strong imino acid effects and it disadvantageously fixes the angle of the polypeptide main chain.

2) Group of Amino Acids having Hydroxymethylene Groups (the ST Group)

Among the neutral polar amino acids, amino acids classified as members of this group have hydroxymethylene groups in the side chain, and this group includes S (Ser, serine) and T (Thr, threonine). Since hydroxyl groups in the S and T side chains are sugar binding sites, such sites are often important for imparting specific activity to a given polypeptide (a protein).

3) Group of Acidic Amino Acids (the DE Group)

Amino acids classified as members of this group have acidic carboxyl groups in the side chain, and this group includes D (Asp, aspartic acid) and E (Glu, glutamic acid). 4) Basic amino acids (the KR group)

Amino acids in this group are basic amino acids, and this group includes K (Lys, lysine) and R (Arg, arginine). K and R are positively charged across a wide pH range and have basic properties. In contrast, H (His, histidine) classified as a basic amino acid is not substantially ionized at pH 7 and, thus, it is not classified as a member of this group.

5) Methylene Group=Polar Group (the DHN Group)

All amino acids in this group comprise a methylene group bound to carbon atoms at position α as side chains and have polar groups bound to the methylene group. Amino acids in this group are very similar to each other in terms of physical sizes of methylene groups, which are non-polar groups, and this group includes N (Asn, asparagine; a polar group is an amide group), D (Asp, aspartic acid; a polar group is a carboxyl group), and H (His, histidine; a polar group is an imidazole group).

6) Dimethylene Group=Polar Group (the EKQR Group)

All amino acids classified as members of this group comprise a linear hydrocarbon with the number of carbon atoms equal to or greater than that of dimethylene groups bound to carbon atoms at position α in the side chains and have polar groups bound to the linear hydrocarbon. Non-polar dimethylene groups are very similar to each other in terms of physical sizes. This group includes E (Glu, glutamic acid; a polar group is a carboxyl group), K (Lys, lysine; a polar group is an amino group), Q (Gln, glutamine; a polar group is an amide group), and R (Arg, arginine, polar groups are imino and amino groups).

7) Aromatic Amino Acids (the FYW Group)

This group includes aromatic amino acids having benzene nuclei in the side chains, and such amino acids have chemical properties peculiar to aromatic compounds. This group includes F (Phe, phenylalanine), Y (Tyr, tyrosine), and W (Trp, tryptophane).

8) Cyclic and Polar Amino Acids (the HY Group)

Amino acids classified as members of this group simultaneously have cyclic structures and polar groups in the side chains. This group includes H (His, histidine; the cyclic construct and a polar group are both imidazole groups) and Y (Tyr, tyrosine; the cyclic structure is a benzene nucleus and a polar group is a hydroxyl group).

An example of the mutant polyhydroxyalkanoic acid synthase gene is a gene comprising an amino acid sequence derived from the amino acid sequence as shown in SEQ ID NO: 2 by deletion, substitution, or addition of 1 or a plurality of amino acid residues, provided that such gene comprises a substitution mutation as described above and encodes a protein having activity of synthesizing polylactic acid using lactyl-CoA as a substrate. In the present invention, the term "a plurality of amino acids" indicate, for example, 1 to 20, preferably 1 to 10, more preferably 1 to 7, further preferably 1 to 5, and particularly preferably 1 to 3 amino acids. A site at which 1 or a plurality of amino acids are to be deleted, substituted, or added is a region excluding the site of substitution described above.

In the present invention, further, the mutant polyhydroxyalkanoic acid synthase gene may encode a protein comprising an amino acid sequence having, for example, 70% or higher, preferably 80% or higher, more preferably 90% or higher, and most preferably 95% or higher sequence similarity with the amino acid sequence as shown in SEQ ID NO: 2, provided that it has the substitution mutation mentioned above, and having activity of synthesizing polylactic acid using lactyl-CoA as a substrate. Sequence similarity is determined by default settings using a database that stores the computer program that implements the BLAST algorithm and the genetic sequence information.

In the present invention, a mutant polyhydroxyalkanoic acid synthase gene may encode a protein comprising a polynucleotide hybridizing under stringent conditions to at least part of the gene comprising the nucleotide sequence as shown in SEQ ID NO: 1, provided that it has the substitution mutation described above, and having activity of synthesizing polylactic acid using lactyl CoA as a substrate.

Under stringent conditions, so-called specific hybrids are formed, but non-specific hybrids are not formed. For example, hybridization is carried out at 45° C. in the presence of 6×SSC (sodium chloride/sodium citrate), and washing is then carried out at 50° C. to 65° C. in the presence of 0.2 to 1×SSC and 0.1% SDS. Alternatively, hybridization is carried out at 65° C. to 70° C. in the presence of 1×SSC, and washing is then carried out at 65° C. to 70° C. in the presence of 0.3×SSC. Hybridization can be carried out via a conventional technique, such as the method described in J. Sambrook et al., Molecular Cloning: A Laboratory Manual, 2nd Ed., Cold Spring Harbor Laboratory, 1989.

Amino acid deletion, substitution, or addition can be carried out by modifying the nucleotide sequence encoding the transcriptional factor in accordance with a method known in the art. Mutation can be introduced into a nucleotide sequence via a conventional technique, such as the Kunkel method or the Gapped Duplex method, or a method in accordance therewith. For example, a mutagenesis kit utilizing site-directed mutagenesis (e.g., Mutant-K or Mutant-G; tradenames, manufactured by TAKARA Bio) or the LA PCR in vitro Mutagenesis Series kit (tradename, manufactured by TAKARA Bio) may be used to introduce mutation. Mutagenesis may be carried out by a method involving the use of chemical mutagens represented by ethylmethane sulfonate (EMS), 5-bromouracil, 2-aminopurine, hydroxylamine, N-methyl-N'-nitro-N-nitrosoguanidine, or other carcinogenic compounds. Alternatively, mutagenesis may be carried out by radiation treatment represented by x rays, alpha rays, beta rays, or gamma rays, or ion beam or ultraviolet treatment.

As described above, the mutant hydroxyalkanoic acid synthase gene occasionally encodes an amino acid sequence that is different from the amino acid sequence shown in SEQ ID NO: 2. In such a case, the numbers indicating the sites of substitution mutation described above would be different from those mentioned above (e.g., position 17 in the amino acid sequence as shown in SEQ ID NO: 2).

Propionyl CoA Transferase Gene

In the present invention, the propionyl CoA transferase gene (hereafter, it is referred to as "the pct gene") is not particularly limited, and a gene derived from *Megasphaera elsdenii* or a gene derived from *Staphylococcus aureus* can be used. SEQ ID NO: 3 shows the nucleotide sequence of the coding region of the pct gene derived from *Megasphaera elsdenii*, and SEQ ID NO: 4 shows the amino acid sequence of the protein encoded by the pct gene. SEQ ID NO: 5 shows the nucleotide sequence of the coding region of the pct gene derived from *Staphylococcus aureus*, and SEQ ID NO: 6 shows the amino acid sequence of the protein encoded by the pct gene. The protein comprising the amino acid sequence as shown in SEQ ID NO: 4 or 6 has propionyl CoA transferase activity, and, in particular, activity of synthesizing lactyl-CoA using lactic acid as a substrate.

In the present invention, the pct gene is not limited to the gene comprising a nucleotide sequence encoding the amino acid sequence as shown in SEQ ID NO: 4 or 6. The pct gene may encode a protein comprising an amino acid sequence derived from the aforementioned amino acid sequence by deletion, substitution, or addition of 1 or a plurality of amino acids and having activity of converting lactic acid into lactyl-CoA. The term "a plurality of amino acids" used herein refers to, for example, 1 to 20, preferably 1 to 10, more preferably 1 to 7, further preferably 1 to 5, and particularly preferably 1 to 3 amino acids.

In the present invention, further, the pct gene may encode a protein comprising an amino acid sequence having, for example, 70% or higher, preferably 80% or higher, more preferably 90% or higher, and most preferably 95% or higher sequence similarity with the amino acid sequence as shown in SEQ ID NO: 4 or 6 and having activity of converting lactic acid into lactyl-CoA. Sequence similarity is determined by default settings using a database that stores a computer program that implements the BLAST algorithm and genetic sequence information.

In the present invention, further, the pct gene may encode a protein comprising a polynucleotide hybridizing under stringent conditions to at least part of the gene comprising the nucleotide sequence as shown in SEQ ID NO: 3 or 5 and having activity of converting lactic acid into lactyl-CoA. The stringent conditions employed herein are as defined in the "mutant hydroxyalkanoic acid synthase gene" section above.

Amino acid deletion, substitution, or addition can be carried out in accordance with the technique described in the "mutant hydroxyalkanoic acid synthase gene" section above.

Host Microorganism

In the present invention, examples of host microorganisms include *Pseudomonas* bacteria such as the *Pseudomonas* sp. 61-3 strain, *Ralstonia* bacteria such as *R. eutropha*, *Bacillus* bacteria such as *Bacillus subtilis*, *Escherichia* bacteria such as *Escherichia coli*, *Corynebacterium* bacteria, *Saccharomyces* yeast strains, such as *Saccharomyces cerevisiae*, and *Candida* yeast strains, such as *Candida maltosa*. Use of *Escherichia coli* as a host microorganism is particularly preferable.

A vector used for introducing the aforementioned gene into a host cell may be any vector, provided that it is capable of autonomous replication in a host cell. A vector in the form of plasmid DNA or phage DNA is preferable. Examples of vectors to be introduced into *E. coli* include plasmid DNAs such as pBR322, pUC18, and pBLuescriptII and phage DNAs such as EMBL3, M13, and λgtII. Examples of vectors to be introduced into yeast include YEp13 and YCp50.

Gene recombination techniques known in the art can be used in order to insert either or both genes mentioned above into a vector. When performing recombination, it is preferable that the relevant gene be ligated to a site downstream of a promoter capable of regulating transcription. Any promoter can be used, provided that it is capable of regulating gene transcription in a host. When *E. coli* host cells are used, for example, trp promoter, lac promoter, PL promoter, PR promoter, or T7 promoter can be used. When yeast host cells are used, for example, gal1 promoter or gal10 promoter can be used.

A terminator sequence, an enhancer sequence, a splicing signal sequence, a poly A addition signal sequence, a ribosome binding sequence (an SD sequence), a selection marker gene, or the like that can be used in a microorganism into which the gene is to be introduced can be ligated to a vector, according to need. Examples of selection marker genes include drug resistance genes, such as ampicillin resistance genes, tetracycline resistance genes, neomycin resistance genes, kanamycin resistance genes, and chloramphenicol resistance genes, genes associated with intracellular biosynthesis of nutrients, such as amino acids or nucleic acids, and genes encoding fluorescent proteins, such as luciferase.

The vector can be introduced into a microorganism by a method known in the art. Examples of methods for introducing a vector into a microorganism include the calcium phosphate method, electroporation, the spheroplast method, the lithium acetate method, the conjugal transfer method, and a method involving the use of calcium ions.

Production of Aliphatic Polyester

Recombinant microorganisms produced via introduction of the mutant hydroxyalkanoic acid synthase gene and the pct gene into host microorganisms are cultured in a medium containing carbon sources, aliphatic polyester is generated and accumulated in the cultured cells or the culture, and aliphatic polyester is recovered from the cultured cells or the culture. The aliphatic polyester of interest can be thus produced. Such recombinant microorganisms synthesize lactic acid from sugar through the sugar metabolic pathway, and the propionyl CoA transferase encoded by the pct gene converts lactic acid into lactyl-CoA. In the recombinant microorganisms, the mutant hydroxyalkanoic acid synthase encoded by the mutant hydroxyalkanoic acid synthase gene synthesizes aliphatic polyester comprising, as a constituent unit, lactic acid using lactyl-CoA as a substrate. Aliphatic polyester may be polylactic acid having lactic acid as a constituent unit (i.e., a homopolymer), or it may be a lactic acid-based copolymer comprising, as constituent units, lactic acid and a hydroxyalkanoic acid other than lactic acid. When synthesizing polylactic acid (a homopolymer), a hydroxyalkanoic acid other than lactic acid is not added to a medium, or biosynthesis pathways for hydroxyalkanoic acids other than lactic acid are lost in the host microorganisms. When synthesizing a lactic acid-based copolymer comprising, as constituent units, lactic acid and hydroxyalkanoic acid other than lactic acid, however, hydroxyalkanoic acid other than lactic acid may be added to a medium, and biosynthesis pathways for hydroxyalkanoic acid other than lactic acid may be imparted to the host microorganisms.

Examples of carbon sources include carbohydrates, such as glucose, fructose, sucrose, and maltose. Alternatively, fat-related substances having 4 or more carbon atoms can be used as carbon sources. Examples of fat-related substances having 4 or more carbon atoms include natural fats, such as corn oil, soybean oil, safflower oil, sunflower oil, olive oil, coconut oil, palm oil, rapeseed oil, fish oil, whale oil, lard, and beef tallow, fatty acids, such as butanoic acid, pentanoic acid, hexanoic acid, octanoic acid, decanoic acid, lauric acid, oleic acid, palmitic acid, linolenic acid, linolic acid, and myristic acid, esters of such fatty acids, alcohols, such as octanol, lauryl alcohol, oleyl alcohol, and palmityl alcohol, and esters of such alcohols.

Examples of nitrogen sources include ammonium salts, such as ammonia, ammonium chloride, ammonium sulfate, and ammonium phosphate, peptone, meat extract, yeast extract, and corn steep liquor. Examples of inorganic matter include monopotassium phosphate, dipotassium phosphate, magnesium phosphate, magnesium sulfate, and sodium chloride.

It is preferable that culture be conducted under aerobic conditions for general shake culture at 25° C. to 37° C. for 24 hours or longer after the mutant hydroxyalkanoic acid synthase gene and the pct gene are expressed. During culture, antibiotics such as kanamycin, ampicillin, or tetracycline may be added to a medium. When either or both the pct gene and the PHA synthase gene are introduced under the control of an inducible promoter, it is preferable that a factor that induces transcription from such promoter be added to a medium and culture then be conducted for 24 hours or longer.

It is particularly preferable that recombinant *E. coli* cells into which the mutant hydroxyalkanoic acid synthase gene and the pct gene have been introduced be cultured to produce polylactic acid. According to such technique, polylactic acid can be produced without the addition of monomer components constituting a polymer of interest, such as lactic acid, to a medium. Thus, such technique is advantageous in terms of production costs.

Aliphatic polyester, such as polylactic acid, may be recovered by a method known in the art. For example, cells are recovered from a culture solution via centrifugation, washed, and then dried. The resulting dry cells are suspended in chloroform, the suspension is heated to extract polyesters of interest and introduce the same into the chloroform fraction, methanol is added to the chloroform solution to precipitate polyesters, and a supernatant is removed via filtration or centrifugation, followed by drying. Thus, purified polyesters can be obtained. Whether or not the recovered polyesters are polylactic acids may be determined via a common technique, such as gas chromatography or nuclear magnetic resonance.

EXAMPLES

Hereafter, the present invention is described in greater detail, although the technical scope of the present invention is not limited to the examples below.

Example 1

Preparation of pTV118N-PCT-C

In Example 1, pTV118N-PCT-C, into which the phaC2 gene derived from the *Alcanivorax borkumensis* SK2 strain and the pct gene derived from *Megasphaera elsdenii* had been introduced, was first prepared based on the pTV118N vector (manufactured by Takara Bio).

The genome of *Megasphaera elsdenii* (ATCC17753) was obtained in accordance with a conventional technique, and the pct gene was then obtained via PCR. The MePCTN: 5'-atgagaaaagtagaaatcattac-3' (SEQ ID NO: 7) primer and the MePCTC: 5'-ttatttttcagtcccatgggaccgtcctg-3' (SEQ ID NO: 8) primer were used to amplify a DNA fragment comprising the pct gene.

Genes were amplified from the genome under the conditions described below. PCR was carried out using an enzyme (KOD plus) via a cycle of 94° C. for 1 minute, 30 cycles of 94° C. for 0.5 minutes, 50° C. for 0.5 minutes, and 72° C. for 2 minutes, and a cycle of 94° C. for 2 minutes. The PCT gene derived from *M. elsdenii* was inserted into a site between EcoR1 and PstI of the pTV118N vector (Takara Bio) to prepare the pTV118N-M.E PCT expression plasmid. Thereafter, the expression plasmid was introduced into *Escherichia coli* W3110.

After the resulting transformed *E. coli* cells were precultured, the resultants were inoculated into a 200-ml LB/21 flask to a concentration of 2% therein, and culture was conducted at 37° C. and 180 rpm for 3 hours. The cells were induced to express with the aid of 10 mM IPTG at OD600 of around 0.5, and culture was conducted at 30° C. and 80 rpm for 6 hours. Subsequently, cells were recovered via centrifugation, cultured at 37° C. in M9 (+1.5% glucose, 10 mM $MgSO_4$, 10 mM calcium pantothenate) (OD=20, 3 ml), and then adequately sampled.

Subsequently, the phaC gene derived from the *Alcanivorax borkumensis* SK2 strain was amplified via two-stage PCR (1st PCR and 2nd PCR). The composition of the reaction solution used for 1st PCR is shown in Table 1.

TABLE 1

| | |
|---|---|
| 10× Buffer for KOD-Plus Ver.2 (final concentration: 1×) | 5 μl |
| 2.5 mM dNTPs (final concentration: 0.25 mM each) | 5 μl |
| 25 mM $MgSO_4$ (final concentration: 1.5 mM) | 2 μl |
| Primer F (10 pmol/μ) (final concentration: 0.3 μM) | 1.5 μl |
| Primer R (10 pmol/μ) (final concentration: 0.3 μM) | 1.5 μl |
| Template DNA genome | 10 to 200 ng |
| KOD-Plus (1 U/μl) (final concentration: 1 U/50 μl) | 1 μl |
| Sterile deionized water | Up to 50 μl |

As Primer F shown in Table 1, *A. borkumensis* F: CATTTCCAGGAGTCGTTGTG (SEQ ID NO: 9) was used, and *A. borkumensis* R: TTGTGCGTAAATCCATTCCC (SEQ ID NO: 10) was used as Primer R. The thermal cycles for the 1st PCR were composed of 30 cycles of 94° C. for 2 minutes, 94° C. for 15 seconds, 45° C. for 30 seconds, and 68° C. for 1 minute and 30 seconds, followed by a cycle of 68° C. for 5 minutes.

The composition of the reaction solution used for 1st PCR is shown in Table 2.

TABLE 2

| | |
|---|---|
| 10× Buffer for KOD-Plus Ver.2 (final concentration: 1×) | 5 μl |
| 2.5 mM dNTPs (final concentration: 0.25 mM each) | 5 μl |
| 25 mM $MgSO_4$ (final concentration: 1.5 mM) | 2 μl |
| Primer F (10 pmol/μ) (final concentration: 0.3 μM) | 1.5 μl |
| Primer R (10 pmol/μ) (final concentration: 0.3 μM) | 1.5 μl |
| Template DNA (1st PCR product, diluted to 1/1,000 after purification) | 1 μl |
| KOD-Plus (1 U/μl) (final concentration: 1 U/50 μl) | 1 μl |
| Sterile deionized water | Up to 50 μl |

As Primer F shown in Table 2, A. borku 2nd Fwd: CCGGTTCGAATCTAGAAATAATTTTGTT-TAACTTTAAGAAGGAGATATACATATGTG GATGGCTA (SEQ ID NO: 11) was used, and A. borku 2nd Rvs: GAACCAGGCGGAACCTGCAGAGATC-CAACCTATGCTGAGCG (SEQ ID NO: 12) was used as the primer R. The thermal cycles for the 2nd PCR were composed of 5 cycles of 94° C. for 2 minutes, 94° C. for 15 seconds, 50° C. for 30 seconds, and 68° C. for 1 minute and 30 seconds, 30 cycles of 94° C. for 15 seconds, 60° C. for 30 seconds, and 68° C. for 1 minute and 30 seconds, and a cycle of 68° C. for 5 minutes.

The obtained DNA fragment was subjected to ligation with the use of the In-Fusion 2.0 Dry-Down PCR Cloning Kit (Clontech Laboratories). Transformation was carried out with the use of ECOS competent *E. coli* JM109 cells (Nippon Gene) in accordance with the protocols. The resulting transformants were cultured in 2 ml of LB-Amp medium, and plasmids were extracted using the QIAprep Spin Miniprep Kit (Qiagen). Sequencing reactions were carried out using the Big Dye Terminator v3.1 Cycle Sequencing Kit (Applied Biosystems), and sequences were confirmed using a DNA sequencer (3100 Genetic Analyzer, Applied Biosystems).

The obtained plasmid was designated as pTV118N-PCT-C.

Preparation of Random Mutant Library

Random mutation was introduced into the phaC gene of the *Alcanivorax borkumensis* SK2 strain included in pTV118N-PCT-C via error-prone PCR. The GeneMorph II Random Mutagenesis Kit (Stratagene) was used as a kit for error-prone PCR. Primer F: CCGGTTCGAATCTA-GAAATAATTTTGTTTAACTTTAAGAAG-GAGATATACATATGTG GATGGCTA (SEQ ID NO: 13) and Primer R: GAACCAGGCGGAACCTGCAGAGATC-CAACCTATGCTGAGCG (SEQ ID NO: 14) were used for error-prone PCR. The composition of the reaction solution used for error-prone PCR is shown in Table 3.

TABLE 3

| | |
|---|---|
| $H_2O$ | 35 μl |
| 10× Buffer for | 5 μl |
| 2 mM dNTPs | 5 μl |
| Primer F (10 pmol) | 1.5 μl |
| Primer R (10 pmol) | 1.5 μl |
| Template | 1 μl |
| KOD-Plus- | 1 μl |
| Total | 50 μl |

Error-prone PCR was carried out through thermal cycles composed of a cycle of 95° C. for 2 minutes and 30 cycles of 95° C. for 30 seconds, 57° C. for 30 seconds, and 72° C. for 1 minute and 20 seconds, followed by a cycle of 72° C. for 10 minutes, and temperature was kept at 4° C. in the end.

The PCR product obtained via error-prone PCR described above was electrophoresed on 0.8% agarose gel, a band of interest (1,215 bp) was confirmed to have been amplified, and the band was cleaved and purified with the use of the MinElute Gel Extraction Kit (Qiagen). Thereafter, the PCR product was digested with PstI and XbaI and purified with the use of the MinElute PCR Purification Kit (Qiagen). Also, pTV118N-PCT-C was digested with PstI and XbaI and electrophoresed on 0.8% agarose gel. After the band of interest (1,215 bp) was confirmed to have been amplified, the band was cleaved and purified with the use of the MinElute Gel Extraction Kit (Qiagen). The fragments were subjected to ligation with the use of the Ligation-Convenience Kit (Nippon Gene) in accordance with the protocols.

Thus, a library containing various mutant phaC genes derived from the *Alcanivorax borkumensis* SK2 strain resulting from introduction of random mutations was prepared.

Transformation

Subsequently, the library obtained above was introduced into *E. coli* competent cells (Origami 2 Competent Cells, Novagene). The library was introduced into *E. coli* cells via electroporation under the conditions described below, so as to enhance the transformation efficiency. Specifically, two Origami strains were precultured in LB agar medium (containing 12.5 µg/ml tetracycline) at 37° C. overnight. Thereafter, 10 ml of LB liquid medium and 12.5 µg/ml tetracycline were introduced into a 100-ml baffled flask, and colonies formed on the LB agar medium were inoculated thereon with the use of toothpicks. Preculture was conducted at 30° C. and 130 rpm overnight.

Subsequently, 1 ml of the preculture solution was inoculated into two 500-ml baffled flasks each containing 100 ml of LB liquid medium and 12.5 µg/ml of tetracycline to conduct main culture. Culture was conducted at 30° C. and 130 rpm for 4.5 hours. Culture was terminated when the OD600 reached 0.4746 and 0.5029. After the completion of culture, the culture product was held for 15 minutes on ice and then fractionated into four 50-ml corning tubes. Centrifugation was then carried out at 2,000 g for 20 minutes (2° C.). After the completion of centrifugation, the supernatant was removed, the precipitate in each tube was suspended in 1 ml of cold sterile water, and 49 ml of cold sterile water was further added thereto. Thereafter, centrifugation was carried out at 2,000 g for 20 minutes (2° C.). After the completion of centrifugation, the supernatant was removed, the precipitate in each tube was suspended in about 1 ml of cold glycerol, and the suspension was recovered in a 2-ml ice-cooled Eppendorf tube. Thereafter, centrifugation was carried out at 2,000 g for 10 minutes (2° C.). After the completion of centrifugation, the supernatant was removed, the precipitate was suspended in 300 ml of 10% glycerol, the suspension was fractionated to each of the ice-cooled Eppendorf tubes in amounts of 20 µl, and the resultants were stored at −80° C.

The competent cells of the 2 obtained Origami strains were subjected to transformation via electroporation. Electroporation was carried out with the use of the Gene Pulser Xcell (BIO-RAD) and a 0.1-cm cuvette (BIO-RAD). The preset protocol "Bacterial 1" was selected (capacitance: 25 µF; resistance: 200Ω; voltage; 1,800 V).

Primary Screening

The thus-obtained transformed *E. coli* cells were applied onto an LB agar medium containing Nile red, culture was conducted at 37° C. for 72 hours, and the resulting colonies that had developed color were identified via primary screening. Nile red is a pigment that turns pink in the presence of a polymer. The LB agar medium containing Nile red was prepared in the following manner. At the outset, 40 g of LB-Agar (Difco) was added to 900 ml of ultrapure water, the resultant was sterilized in an autoclave, the sterilized product was cooled to around room temperature, and 100 ml of 20% D-glucose, 2 ml of 100 mg/ml ampicillin (Sigma), 1 ml of 12.5 µg/ml tetracycline (Sigma), 100 µl of 1 M IPTG (Nacalai Tesque), and 1 ml of 5 mg/ml Nile red (Nacalai Tesque) were added to bring the total amount of the mixture to 1 liter. The resulting solution was fractionated to petri dishes in amounts of 15 ml each and then allowed to cool and solidify.

Secondary Screening

Among the colored colonies identified via primary screening above, 47 colonies exhibiting particularly strong expression intensity were cultured, and the extent of polymer production was analyzed. Experiment was carried out by culturing *E. coli* cells into which only the pct genes were introduced and wild-type strains into which no foreign genes were introduced in the same manner, and the amount of polymer production was analyzed.

Specifically, colonies were collected by scraping, inoculated into a test tube containing 2 ml of LB liquid medium (containing 100 µg/ml ampicillin), and shake-cultured at 37° C. until OD600 reached 0.6 to 1.0. Such procedure was carried out as pre-culture.

Subsequently, 200 ml of M9 medium to which ampicillin at a final concentration of 100 mg/ml and IPTG at a final concentration of 0.1 mM had been added was introduced into a 500-ml baffled triangular flask, and 2 ml of the preculture solution was added thereto. Culture was then conducted at 30° C. and 130 rpm for 48 hours. Such procedure was carried out as main culture. The composition of M9 medium (per liter) is shown in Table 4.

TABLE 4

| | |
|---|---|
| 10× M9 salts* | 100 ml |
| 1M MgSO$_4$ | 2 ml |
| 20% Glucose | 100 ml |
| 1M CaCl$_2$ | 0.1 ml |
| 1% thiamine | 1 ml |

(10× M9 salts: 128 g of NaHPO$_4$·7H$_2$O, 30 g of KH$_2$PO$_4$, 2.6 g of NaCl, 5.0 g of NH$_4$Cl)

After the completion of main culture, the culture solution was transferred to a 50-ml Corning tube, cells were harvested at 3,000 rpm for 15 minutes, the supernatant was discarded, and the resultant was stored in a freezer at −80° C. overnight for freezing. Thereafter, the resultant was subjected to lyophilization with the use of a lyophilizer for 2 days. Thereafter, 100 mg of dry cells were transferred to a pressure-resistant reaction tube, and 1.6 ml of chloroform was added. Further, 1.6 ml of a mixed solution of methanol and sulfuric acid (a ratio of methanol to sulfuric acid is 17:3 by volume) was added, and the resultant was subjected to reflux in a water bath set at 95° C. for 3 hours. Thereafter, the pressure-resistant reaction tube was removed and cooled to room temperature, and the solution therein was transferred to a test tube. Further, 0.8 ml of ultrapure water was added to the test tube, the content of the test tube was mixed using a vortex mixer, and the mixture was allowed to stand. After the mixture was allowed to stand for a sufficient period of time, the underlying chloroform layer was fractionated with the use of a Pasteur pipette. The chloroform layer was filtered through an organic-solvent-resistant filter (mesh size: 0.2 µm) and transferred to a vial bottle for GC-MS to prepare a sample for analysis.

As a GC-MS apparatus, the HP 6890 Series GC system equipped with a 5973 Mass Selective Detector (Agilent Technologies) was used. The BD-1 122-1063 column (inner diameter: 0.25 mm; length: 60 m; membrane thickness: 1 µm, Agilent Technologies) was used. Temperature was kept at 120° C. for 5 minutes, raised to 200° C. at 10° C./min, raised to 300° C. at 20° C./min, and then kept at that temperature for 8 minutes.

Also, the nucleotide sequence of the phaC gene, which had been introduced into a plurality of transformed *E. coli* cells producing significantly higher amounts of lactic acid polymers than control samples, was examined in order to identify the site of mutation. Nucleotide sequencing was carried out by extracting plasmids from the transformed *E. coli* cells using the QIAprep Spin Miniprep Kit (QIAGEN) in accordance with the protocols. Thereafter, sequencing reactions were carried out using the Big Dye Terminator v3.1 Cycle Sequencing Kit (Applied Biosystems) and the primers shown below, and the nucleotide sequence was determined using the DNA sequencer (3100 Genetic Analyzer, Applied Biosystems). The amino acid sequence of the protein encoded by the phaC gene into which mutation had been introduced was identified based thereon, and substitution mutation at the amino acid level was identified.

```
Primers for sequencing reactions
                              (SEQ ID NO: 15)
UNIFWD S1:           GTTTAACTTTAAGAAGG (SEQ ID NO: 16)
12Aboku-Y S113:      CACCTACGTCAATCGCT (SEQ ID NO: 17)
UNIRVS S2:           ACCAGGCGGAACCTGCA (SEQ ID NO: 18)
12Aboku-Y S115:      ATCCAAGTGCCAGGAGG
```

Figure 2:
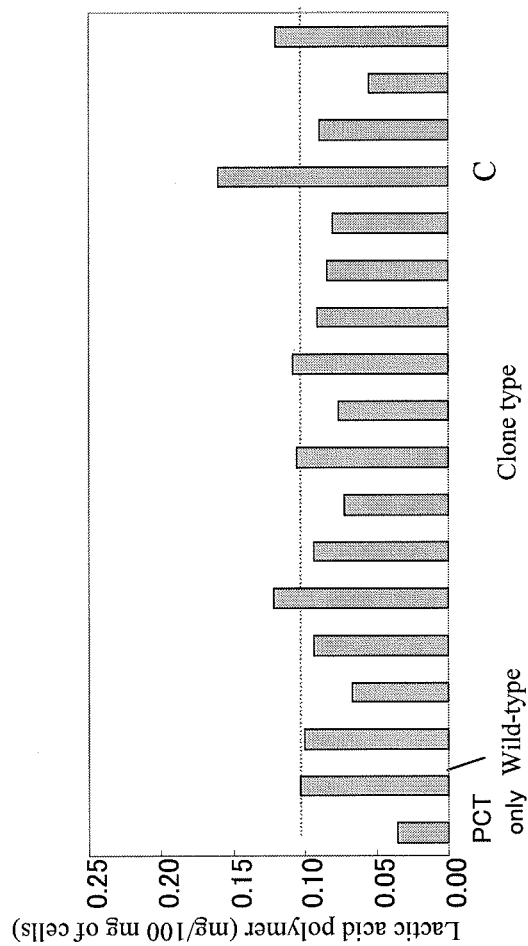
FIG. 2 is a characteristic diagram showing the amount of polylactic acids produced with the use of the transformed *E. coli* cells prepared in the examples.
Figure 3:
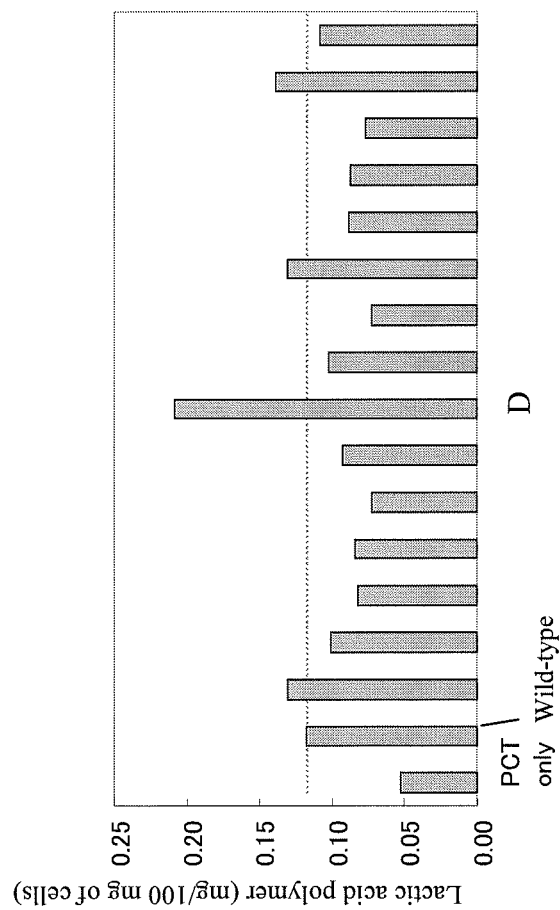
FIG. 3 is a characteristic diagram showing the amount of polylactic acids produced with the use of the transformed *E. coli* cells prepared in the examples.

The results of a comparison of the polylactic acid productivity of transformed *E. coli* cells are shown in FIGS. 1 to 3. Also, the extent of polylactic acid production by the transformed *E. coli* cells shown in FIGS. 1 to 3 is shown in Tables 5 to 7. In Tables 5 to 7, the results of GC-MS analysis are shown in terms of the amount of lactic acid polymers (mg) relative to 100 mg of cells.

TABLE 5

Results of amino acid sequence analysis

| | Results of GC-MS analysis | When wild-type is 1 | Amino acid sequence mutation | |
|---|---|---|---|---|
| | | | Number | Site of mutation |
| Wild-type | 0.120 | — | | |
| | 0.147 | 1.23 | 1 | N291Y |
| | 0.121 | 1.01 | | |
| | 0.120 | 1.00 | 1 | L230Q |
| | 0.114 | 0.95 | | |
| | 0.130 | 1.08 | 2 | S119T, E257G |
| | 0.144 | 1.20 | 1 | L192H |
| | 0.146 | 1.22 | 1 | L222Q |
| A | 0.205 | 1.71 | 1 | P239L |
| | 0.146 | 1.22 | 1 | A196P |
| | 0.148 | 1.23 | 1 | N96T |
| | 0.140 | 1.17 | 2 | M104L, T237I |
| | 0.085 | 0.71 | 5 | K5N, V31L, H106Q, L232P, D332G |
| | 0.108 | 0.90 | | |
| B | 0.171 | 1.43 | 1 | V131I |
| | 0.126 | 1.05 | | |
| | 0.152 | 1.27 | 2 | P217S, V242M |

TABLE 6

Results of amino acid sequence analysis

| | Results of GC-MS analysis | When wild-type is 1 | Amino acid sequence mutation | |
|---|---|---|---|---|
| | | | Number | Site of mutation |
| Wild-type | 0.103 | — | | |
| | 0.101 | 0.98 | | |
| | 0.068 | 0.66 | | |
| | 0.093 | 0.90 | 2 | A4T, E346G |
| | 0.121 | 1.17 | 4 | K9T, I213N, I250N, L289H |
| | 0.093 | 0.90 | | |
| | 0.073 | 0.71 | | |
| | 0.106 | 1.03 | | |
| | 0.077 | 0.75 | | |
| | 0.108 | 1.05 | | |
| | 0.091 | 0.88 | | |
| | 0.084 | 0.82 | | |
| | 0.081 | 0.79 | | |
| C | 0.160 | 1.55 | 3 | H17L, P71S, M205T |
| | 0.090 | 0.87 | | |
| | 0.055 | 0.53 | | |
| | 0.121 | 1.17 | 3 | I86M, H106R, I225N |

TABLE 7

Results of amino acid sequence analysis

| | Results of GC-MS analysis | When wild-type is 1 | Amino acid sequence mutation | |
|---|---|---|---|---|
| | | | Number | Site of mutation |
| Wild-type | 0.117 | — | | |
| | 0.130 | 1.11 | | |
| | 0.101 | 0.86 | | |
| | 0.082 | 0.70 | | |
| | 0.085 | 0.73 | | |
| | 0.072 | 0.62 | | |
| | 0.092 | 0.79 | | |
| D | 0.208 | 1.78 | 1 | L230M |
| | 0.102 | 0.87 | | |
| | 0.072 | 0.62 | | |
| | 0.131 | 1.12 | | |
| | 0.089 | 0.76 | | |
| | 0.087 | 0.74 | | |
| | 0.077 | 0.66 | | |
| | 0.139 | 1.19 | 2 | L78I, Q244R |
| | 0.108 | 0.92 | | |

As shown in FIGS. 1 to 3 and Tables 5 to 7, most of the colored colonies selected via primary screening exhibited a degree of polylactic acid production approximately equal to or 1.2 times greater than that of wild-type cells. However, the transformed *E. coli* cells designated as A, B, C, and D in the figures and the tables exhibited a degree of polylactic acid production that increased to approximately 1.5 times greater than the figures for wild-type cells, unlike other transformed *E. coli* cells. That is, transformed *E. coli* cells that are excellent in terms of the degree of polylactic acid production were obtained in this example. As a result of nucleotide sequence analysis of the mutant pha2 gene into which the transformed *E. coli* cells that are excellent in terms of the degree of polylactic acid production had been introduced, activity of polylactic acid synthesis (i.e., polymerization activity) was found to be remarkably enhanced via substitution of a histidine residue at position 17 determined based on the methionine residue at the N terminus with leucine (H17L), substitution of a proline residue at position 71 with serine (P71S), substitution of a valine residue at position 131 with isoleucine (V131I), substitution of a methionine residue at position 205 with threonine (M205T), substitution of a leucine residue at position 230 with methionine (L230M), or substitution of a proline residue at position 239 with leucine (P239L) in the polyhydroxyalkanoic acid synthase encoded by the pha2 gene derived from *Alcanivorax borkumensis* SK2 as shown in SEQ ID NO: 2.

In particular, the mutant polyhydroxyalkanoic acid synthase having a single mutation of P239L or L230M exhibited a degree of polylactic acid production as great as 1.7 times greater than the figures for wild-type cells in terms of synthesizing activity. Such results demonstrate that a mutant polyhydroxyalkanoic acid synthase having a single mutation of P239L or L230M is very useful since it exhibits the strongest polylactic acid synthesis activity; i.e., polymerization activity.

The invention claimed is:

1. A nucleic acid encoding a polypeptide having an amino sequence of SEQ ID NO:2, wherein the proline residue at position 239 is substituted with leucine.

2. A nucleic acid encoding a polypeptide having an amino sequence of SEQ ID NO:2, wherein the valine residue at position 131 is substituted with isoleucine.

3. A nucleic acid encoding a polypeptide having an amino sequence of SEQ ID NO:2, wherein the histidine residue at position 17 is substituted with leucine, the proline residue at position 71 is substituted with serine, and the methionine residue at position 205 is substituted with threonine.

4. A nucleic acid encoding a polypeptide having an amino sequence of SEQ ID NO:2, wherein the leucine residue at position 230 is substituted with methionine.

5. An expression vector comprising the nucleic acid according to claim 1.

6. The expression vector according to claim 5, which further comprises a nucleic acid encoding an enzyme that converts hydroxyalkanoic acid into hydroxyalkanoic acid CoA, wherein the enzyme is a propionyl CoA transferase derived from *Megasphaera elsdenii* or *Staphylococcus aureus*.

7. A recombinant microorganism into which the nucleic acid according to claim 1 and a nucleic acid encoding an enzyme that converts hydroxyalkanoic acid into hydroxyalkanoic acid CoA have been introduced, wherein the enzyme is a propionyl CoA transferase derived from *Megasphaera elsdenii* or *Staphylococcus aureus*.

8. A method for producing aliphatic polyester comprising culturing the recombinant microorganism according to claim 7 in a medium containing a carbon source and recovering aliphatic polyester.

9. The method for producing aliphatic polyester according to claim 8, wherein the aliphatic polyester to be recovered is aliphatic polyester having the polylactic acid backbone.

10. The method for producing aliphatic polyester according to claim 9, wherein the aliphatic polyester to be recovered is polylactic acid.

11. The method for producing aliphatic polyester according to claim 8, wherein lactic acid is not added to a medium when culturing the recombinant microorganism.

12. The method for producing aliphatic polyester according to claim 8, wherein the carbon source is a carbohydrate or a fat-related substance.

13. The method for producing aliphatic polyester according to claim 4, wherein the carbohydrate is selected from the group consisting of glucose, fructose, sucrose, and maltose.

14. The method for producing aliphatic polyester according to claim 8, wherein the fat-related substance is selected from the group consisting of corn oil, soybean oil, safflower oil, sunflower oil, olive oil, coconut oil, palm oil, rapeseed oil, fish oil, whale oil, lard, beef tallow, fatty acids, butanoic acid, pentanoic acid, hexanoic acid, octanoic acid, decanoic acid, lauric acid, oleic acid, palmitic acid, linolenic acid, linolic acid, and myristic acid, esters of fatty acids, alcohols, octanol, lauryl alcohol, oleyl alcohol, palmityl alcohol, and esters of alcohols.

15. The method for producing aliphatic polyester according to claim 8, wherein the nucleic acid encoding the polypeptide having an amino sequence of SEQ ID NO:2, wherein the proline residue at position 239 is substituted with leucine, and the nucleic acid encoding an enzyme that converts hydroxyalkanoic acid into hydroxyalkanoic acid CoA are under the control of an inducible promoter, and the culturing is in the presence of a factor that induces transcription from the promoter.

* * * * *

SEQUENCE LISTING

<160> NUMBER OF SEQ ID NOS: 18

<210> SEQ ID NO 1
<211> LENGTH: 1134
<212> TYPE: DNA
<213> ORGANISM: Alcanivorax borkumensis SK2
<220> FEATURE:
<221> NAME/KEY: CDS
<222> LOCATION: (1)..(1134)

<400> SEQUENCE: 1

```
atg tgg atg gct aaa tca cga tta aaa aaa agt ctg cgt gcc gtt ggc        48
Met Trp Met Ala Lys Ser Arg Leu Lys Lys Ser Leu Arg Ala Val Gly
1               5                   10                  15 cac att gtt gag cgc agg cgc cac ccg caa cgc ttt atc cac gtg gat        96
His Ile Val Glu Arg Arg Arg His Pro Gln Arg Phe Ile His Val Asp
                20                  25                  30 aaa tgc ccg tgg gag gaa gtg tat cgt gac ggc atc atg gcg gta cgc       144
Lys Cys Pro Trp Glu Glu Val Tyr Arg Asp Gly Ile Met Ala Val Arg
            35                  40                  45 cat tac agc cta ccc tct acg gct acg gct aaa atc tcg att aac gat       192
His Tyr Ser Leu Pro Ser Thr Ala Thr Ala Lys Ile Ser Ile Asn Asp
        50                  55                  60 gat ttc ctg cct gtt tcc cct gta aaa cac cgc atc ccc ctt ttg ttg       240
Asp Phe Leu Pro Val Ser Pro Val Lys His Arg Ile Pro Leu Leu Leu
65                  70                  75                  80 gtt ccg gcg ctg ggt att cat tgc tgg acc tac gat ttg atg cca aac       288
Val Pro Ala Leu Gly Ile His Cys Trp Thr Tyr Asp Leu Met Pro Asn
                85                  90                  95 cga tcc atg gtc cgt tat ctt atg gct cat ggt tat gag gtc tat ctg       336
Arg Ser Met Val Arg Tyr Leu Met Ala His Gly Tyr Glu Val Tyr Leu
                100                 105                 110 gtt gac tgg gga aag cct tca gat acc gac tgc agc cta aat ttg gac       384
Val Asp Trp Gly Lys Pro Ser Asp Thr Asp Cys Ser Leu Asn Leu Asp
            115                 120                 125 acc tac gtc aat cgc tgg ttg ccc tct gca gtt gaa aca gtg cga aaa       432
Thr Tyr Val Asn Arg Trp Leu Pro Ser Ala Val Glu Thr Val Arg Lys
        130                 135                 140 cat gcg cag acc gaa acc atc aac atg atg ggc tac tgc atg ggc gga       480
His Ala Gln Thr Glu Thr Ile Asn Met Met Gly Tyr Cys Met Gly Gly
145                 150                 155                 160 ctg ctg tgc cta atg tat cta ggc ggc cac agt gat gcg ccg gtg cgt       528
Leu Leu Cys Leu Met Tyr Leu Gly Gly His Ser Asp Ala Pro Val Arg
                165                 170                 175 agc ctg att acc att gcc agc ccc gtg aat ttt cac aaa agc ggc ctt       576
Ser Leu Ile Thr Ile Ala Ser Pro Val Asn Phe His Lys Ser Gly Leu
                180                 185                 190 ttc ggc aag gcc tta ggg ctg gcg gct atc cct gcc atg cag ctc cat       624
Phe Gly Lys Ala Leu Gly Leu Ala Ala Ile Pro Ala Met Gln Leu His
            195                 200                 205 gac cgg ttt aag att cgt ctt gaa ccg ctc agt gat aag cta ttc cat       672
Asp Arg Phe Lys Ile Arg Leu Glu Pro Leu Ser Asp Lys Leu Phe His
        210                 215                 220 atc cct gcc agc ctc ctg gca ctt gga ttc aag atg acc aac cct cca       720
Ile Pro Ala Ser Leu Leu Ala Leu Gly Phe Lys Met Thr Asn Pro Pro
225                 230                 235                 240 gga gtg gtg cag gcc tac atg gat ctg atc cgc aat atc ggt gac cga       768
Gly Val Val Gln Ala Tyr Met Asp Leu Ile Arg Asn Ile Gly Asp Arg
                245                 250                 255 gaa tac gtc acc gag tac atg acc atg ggg cag tgg ttt aac gac atg       816
Glu Tyr Val Thr Glu Tyr Met Thr Met Gly Gln Trp Phe Asn Asp Met
```

```
                          260                 265                 270
gtc gat tat cct ggt gcg gtg gtg cgt gag gtt atc gag aaa atg ctt      864
Val Asp Tyr Pro Gly Ala Val Val Arg Glu Val Ile Glu Lys Met Leu
        275                 280                 285 ctt gcc aat agt ctg gcc aaa ggc aaa atc cac atc ggc ggc cgc agc      912
Leu Ala Asn Ser Leu Ala Lys Gly Lys Ile His Ile Gly Gly Arg Ser
        290                 295                 300 gtg gat ttc tca tcc att cag cag gat ttg ctc gct ttt gca ggc att      960
Val Asp Phe Ser Ser Ile Gln Gln Asp Leu Leu Ala Phe Ala Gly Ile
305                 310                 315                 320 acc gac aac att gtc agt ctt cga gcc gca cgg gat atc atc caa ctt     1008
Thr Asp Asn Ile Val Ser Leu Arg Ala Ala Arg Asp Ile Ile Gln Leu
                325                 330                 335 gtc ggc agc aaa gaa aaa cgc ttc gag gaa gta cct ggc gga cac gca     1056
Val Gly Ser Lys Glu Lys Arg Phe Glu Glu Val Pro Gly Gly His Ala
        340                 345                 350 ggc gct ttt tgc ggt tcg aaa gca cct tcc aat gcc tgg cgc atc agc     1104
Gly Ala Phe Cys Gly Ser Lys Ala Pro Ser Asn Ala Trp Arg Ile Ser
        355                 360                 365 gct gac tgg ttg gcg gcg cgc tca gca tag                             1134
Ala Asp Trp Leu Ala Ala Arg Ser Ala
        370                 375

<210> SEQ ID NO 2
<211> LENGTH: 377
<212> TYPE: PRT
<213> ORGANISM: Alcanivorax borkumensis SK2

<400> SEQUENCE: 2

Met Trp Met Ala Lys Ser Arg Leu Lys Lys Ser Leu Arg Ala Val Gly
1               5                   10                  15

His Ile Val Glu Arg Arg His Pro Gln Arg Phe Ile His Val Asp
                20                  25                  30

Lys Cys Pro Trp Glu Glu Val Tyr Arg Asp Gly Ile Met Ala Val Arg
            35                  40                  45

His Tyr Ser Leu Pro Ser Thr Ala Thr Ala Lys Ile Ser Ile Asn Asp
        50                  55                  60

Asp Phe Leu Pro Val Ser Pro Val Lys His Arg Ile Pro Leu Leu Leu
65                  70                  75                  80

Val Pro Ala Leu Gly Ile His Cys Trp Thr Tyr Asp Leu Met Pro Asn
                85                  90                  95

Arg Ser Met Val Arg Tyr Leu Met Ala His Gly Tyr Glu Val Tyr Leu
            100                 105                 110

Val Asp Trp Gly Lys Pro Ser Asp Thr Asp Cys Ser Leu Asn Leu Asp
        115                 120                 125

Thr Tyr Val Asn Arg Trp Leu Pro Ser Ala Val Glu Thr Val Arg Lys
    130                 135                 140

His Ala Gln Thr Glu Thr Ile Asn Met Met Gly Tyr Cys Met Gly Gly
145                 150                 155                 160

Leu Leu Cys Leu Met Tyr Leu Gly Gly His Ser Asp Ala Pro Val Arg
                165                 170                 175

Ser Leu Ile Thr Ile Ala Ser Pro Val Asn Phe His Lys Ser Gly Leu
            180                 185                 190

Phe Gly Lys Ala Leu Gly Leu Ala Ala Ile Pro Ala Met Gln Leu His
        195                 200                 205

Asp Arg Phe Lys Ile Arg Leu Glu Pro Leu Ser Asp Lys Leu Phe His
    210                 215                 220
```

```
Ile Pro Ala Ser Leu Leu Ala Leu Gly Phe Lys Met Thr Asn Pro Pro
225                 230                 235                 240

Gly Val Val Gln Ala Tyr Met Asp Leu Ile Arg Asn Ile Gly Asp Arg
            245                 250                 255

Glu Tyr Val Thr Glu Tyr Met Thr Met Gly Gln Trp Phe Asn Asp Met
                260                 265                 270

Val Asp Tyr Pro Gly Ala Val Val Arg Glu Val Ile Glu Lys Met Leu
            275                 280                 285

Leu Ala Asn Ser Leu Ala Lys Gly Lys Ile His Ile Gly Gly Arg Ser
        290                 295                 300

Val Asp Phe Ser Ser Ile Gln Gln Asp Leu Leu Ala Phe Ala Gly Ile
305                 310                 315                 320

Thr Asp Asn Ile Val Ser Leu Arg Ala Ala Arg Asp Ile Ile Gln Leu
                325                 330                 335

Val Gly Ser Lys Glu Lys Arg Phe Glu Glu Val Pro Gly Gly His Ala
            340                 345                 350

Gly Ala Phe Cys Gly Ser Lys Ala Pro Ser Asn Ala Trp Arg Ile Ser
        355                 360                 365

Ala Asp Trp Leu Ala Ala Arg Ser Ala
370                 375

<210> SEQ ID NO 3
<211> LENGTH: 1554
<212> TYPE: DNA
<213> ORGANISM: Megasphaera elsdenii
<220> FEATURE:
<221> NAME/KEY: CDS
<222> LOCATION: (1)..(1554)

<400> SEQUENCE: 3 atg aga aaa gta gaa atc att aca gct gaa caa gca gct cag ctc gta       48
Met Arg Lys Val Glu Ile Ile Thr Ala Glu Gln Ala Ala Gln Leu Val
1               5                   10                  15 aaa gac aac gac acg att acg tct atc ggc ttt gtc agc agc gcc cat       96
Lys Asp Asn Asp Thr Ile Thr Ser Ile Gly Phe Val Ser Ser Ala His
                20                  25                  30 ccg gaa gca ctg acc aaa gct ttg gaa aaa cgg ttc ctg gac acg aac      144
Pro Glu Ala Leu Thr Lys Ala Leu Glu Lys Arg Phe Leu Asp Thr Asn
            35                  40                  45 acc ccg cag aac ttg acc tac atc tat gca ggc tct cag ggt aaa cgc      192
Thr Pro Gln Asn Leu Thr Tyr Ile Tyr Ala Gly Ser Gln Gly Lys Arg
        50                  55                  60 gat ggc cgt gcc gct gaa cat ctg gca cac aca ggc ctt ttg aaa cgc      240
Asp Gly Arg Ala Ala Glu His Leu Ala His Thr Gly Leu Leu Lys Arg
65                  70                  75                  80 gcc atc atc ggt cac tgg cag act gta ccg gct atc ggt aaa ctg gct      288
Ala Ile Ile Gly His Trp Gln Thr Val Pro Ala Ile Gly Lys Leu Ala
                85                  90                  95 gtc gaa aac aag att gaa gct tac aac ttc tcg cag ggc acg ttg gtc      336
Val Glu Asn Lys Ile Glu Ala Tyr Asn Phe Ser Gln Gly Thr Leu Val
            100                 105                 110 cac tgg ttc cgc gcc ttg gca ggt cat aag ctc ggc gtc ttc acc gac      384
His Trp Phe Arg Ala Leu Ala Gly His Lys Leu Gly Val Phe Thr Asp
        115                 120                 125 atc ggt ctg gaa act ttc ctc gat ccc gta cag ctc ggc ggc aag ctc      432
Ile Gly Leu Glu Thr Phe Leu Asp Pro Arg Gln Leu Gly Gly Lys Leu
    130                 135                 140 aat gac gta acc aaa gaa gac ctc gtc aaa ctg atc gaa gtc gat ggt      480
```

```
Asn Asp Val Thr Lys Glu Asp Leu Val Lys Leu Ile Glu Val Asp Gly
145                 150                 155                 160 cat gaa cag ctt ttc tac ccg acc ttc ccg gtc aac gta gct ttc ctc      528
His Glu Gln Leu Phe Tyr Pro Thr Phe Pro Val Asn Val Ala Phe Leu
                    165                 170                 175 cgc ggt acg tat gct gat gaa tcc ggc aat atc acc atg gac gaa gaa      576
Arg Gly Thr Tyr Ala Asp Glu Ser Gly Asn Ile Thr Met Asp Glu Glu
                180                 185                 190 atc ggg cct ttc gaa agc act tcc gta gcc cag gcc gtt cac aac tgt      624
Ile Gly Pro Phe Glu Ser Thr Ser Val Ala Gln Ala Val His Asn Cys
            195                 200                 205 ggc ggt aaa gtc gtc gtc cag gtc aaa gac gtc gtc gct cac ggc agc      672
Gly Gly Lys Val Val Val Gln Val Lys Asp Val Val Ala His Gly Ser
        210                 215                 220 ctg gat ccg cgc atg gtc aaa atc cct ggc atc tat gtc gac tat gtt      720
Leu Asp Pro Arg Met Val Lys Ile Pro Gly Ile Tyr Val Asp Tyr Val
225                 230                 235                 240 gtc gta gct gct ccg gaa gac cat cag cag act tat gac tgc gaa tat      768
Val Val Ala Ala Pro Glu Asp His Gln Gln Thr Tyr Asp Cys Glu Tyr
                    245                 250                 255 gat ccg tcc ctt agc ggc gaa cat cgt gct cct gaa ggc gct gct gac      816
Asp Pro Ser Leu Ser Gly Glu His Arg Ala Pro Glu Gly Ala Ala Asp
                260                 265                 270 gca gct ctc ccc atg agc gct aag aaa atc atc ggc cgc cgc ggt gct      864
Ala Ala Leu Pro Met Ser Ala Lys Lys Ile Ile Gly Arg Arg Gly Ala
            275                 280                 285 ttg gaa ttg acc gaa aac gct gtc gtc aac ctc ggc gtc ggc gct ccg      912
Leu Glu Leu Thr Glu Asn Ala Val Val Asn Leu Gly Val Gly Ala Pro
        290                 295                 300 gaa tac gtt gct tcc gtt gcc ggt gaa gaa ggt atc gct gat acc att      960
Glu Tyr Val Ala Ser Val Ala Gly Glu Glu Gly Ile Ala Asp Thr Ile
305                 310                 315                 320 acc ttg acc gtc gaa ggt ggc gct atc ggt ggt gta ccg cag ggc ggt     1008
Thr Leu Thr Val Glu Gly Gly Ala Ile Gly Gly Val Pro Gln Gly Gly
                    325                 330                 335 gcc cgc ttc ggt tcg tcc cgt aat gct gat gcc atc atc gac cat act     1056
Ala Arg Phe Gly Ser Ser Arg Asn Ala Asp Ala Ile Ile Asp His Thr
                340                 345                 350 tac cag ttc gac ttc tat gat ggc ggt ggt ctg gac atc gct tac ctc     1104
Tyr Gln Phe Asp Phe Tyr Asp Gly Gly Gly Leu Asp Ile Ala Tyr Leu
            355                 360                 365 ggc ctg gct cag tgc gat ggt tcg ggc aac atc aac gtc agc aag ttc     1152
Gly Leu Ala Gln Cys Asp Gly Ser Gly Asn Ile Asn Val Ser Lys Phe
        370                 375                 380 ggt act aac gtt gcc ggc tgt ggc ggt ttc ccc aac att tcc cag cag     1200
Gly Thr Asn Val Ala Gly Cys Gly Gly Phe Pro Asn Ile Ser Gln Gln
385                 390                 395                 400 aca ccg aat gtt tac ttc tgc ggc acc ttc acg gct ggc ggc ttg aaa     1248
Thr Pro Asn Val Tyr Phe Cys Gly Thr Phe Thr Ala Gly Gly Leu Lys
                    405                 410                 415 atc gct gtc gaa gac ggc aaa gtc aag atc ctc cag gaa ggc aaa gcc     1296
Ile Ala Val Glu Asp Gly Lys Val Lys Ile Leu Gln Glu Gly Lys Ala
                420                 425                 430 aag aag ttc atc aaa gct gtc gac cag atc act ttc aac ggt tct tat     1344
Lys Lys Phe Ile Lys Ala Val Asp Gln Ile Thr Phe Asn Gly Ser Tyr
            435                 440                 445 gca gcc cgc aac ggc aaa cat gtt ctc tac atc acg gaa cgc tgc gta     1392
Ala Ala Arg Asn Gly Lys His Val Leu Tyr Ile Thr Glu Arg Cys Val
        450                 455                 460
```

```
ttt gaa ctg acc aaa gaa ggc ttg aaa ctc atc gaa gtc gca ccg ggc    1440
Phe Glu Leu Thr Lys Glu Gly Leu Lys Leu Ile Glu Val Ala Pro Gly
465                 470                 475                 480 atc gat att gaa aaa gat atc ctc gct cac atg gac ttc aag ccg atc    1488
Ile Asp Ile Glu Lys Asp Ile Leu Ala His Met Asp Phe Lys Pro Ile
                485                 490                 495 att gat aat ccg aaa ctc atg gat gcc cgc ctc ttc cag gac ggt ccc    1536
Ile Asp Asn Pro Lys Leu Met Asp Ala Arg Leu Phe Gln Asp Gly Pro
            500                 505                 510 atg gga ctg aaa aaa taa                                            1554
Met Gly Leu Lys Lys
            515

<210> SEQ ID NO 4
<211> LENGTH: 517
<212> TYPE: PRT
<213> ORGANISM: Megasphaera elsdenii

<400> SEQUENCE: 4

Met Arg Lys Val Glu Ile Ile Thr Ala Glu Gln Ala Ala Gln Leu Val
1               5                   10                  15

Lys Asp Asn Asp Thr Ile Thr Ser Ile Gly Phe Val Ser Ser Ala His
            20                  25                  30

Pro Glu Ala Leu Thr Lys Ala Leu Glu Lys Arg Phe Leu Asp Thr Asn
        35                  40                  45

Thr Pro Gln Asn Leu Thr Tyr Ile Tyr Ala Gly Ser Gln Gly Lys Arg
    50                  55                  60

Asp Gly Arg Ala Ala Glu His Leu Ala His Thr Gly Leu Leu Lys Arg
65                  70                  75                  80

Ala Ile Ile Gly His Trp Gln Thr Val Pro Ala Ile Gly Lys Leu Ala
                85                  90                  95

Val Glu Asn Lys Ile Glu Ala Tyr Asn Phe Ser Gln Gly Thr Leu Val
            100                 105                 110

His Trp Phe Arg Ala Leu Ala Gly His Lys Leu Gly Val Phe Thr Asp
        115                 120                 125

Ile Gly Leu Glu Thr Phe Leu Asp Pro Arg Gln Leu Gly Gly Lys Leu
    130                 135                 140

Asn Asp Val Thr Lys Glu Asp Leu Val Lys Leu Ile Glu Val Asp Gly
145                 150                 155                 160

His Glu Gln Leu Phe Tyr Pro Thr Phe Pro Val Asn Val Ala Phe Leu
                165                 170                 175

Arg Gly Thr Tyr Ala Asp Glu Ser Gly Asn Ile Thr Met Asp Glu Glu
            180                 185                 190

Ile Gly Pro Phe Glu Ser Thr Ser Val Ala Gln Ala Val His Asn Cys
        195                 200                 205

Gly Gly Lys Val Val Val Gln Val Lys Asp Val Val Ala His Gly Ser
    210                 215                 220

Leu Asp Pro Arg Met Val Lys Ile Pro Gly Ile Tyr Val Asp Tyr Val
225                 230                 235                 240

Val Val Ala Ala Pro Glu Asp His Gln Gln Thr Tyr Asp Cys Glu Tyr
                245                 250                 255

Asp Pro Ser Leu Ser Gly Glu His Arg Ala Pro Glu Gly Ala Ala Asp
            260                 265                 270

Ala Ala Leu Pro Met Ser Ala Lys Lys Ile Ile Gly Arg Arg Gly Ala
        275                 280                 285

Leu Glu Leu Thr Glu Asn Ala Val Val Asn Leu Gly Val Gly Ala Pro
```

```
                290                 295                 300
Glu Tyr Val Ala Ser Val Ala Gly Glu Glu Gly Ile Ala Asp Thr Ile
305                 310                 315                 320

Thr Leu Thr Val Glu Gly Gly Ala Ile Gly Gly Val Pro Gln Gly Gly
                325                 330                 335

Ala Arg Phe Gly Ser Ser Arg Asn Ala Asp Ala Ile Ile Asp His Thr
            340                 345                 350

Tyr Gln Phe Asp Phe Tyr Asp Gly Gly Leu Asp Ile Ala Tyr Leu
        355                 360                 365

Gly Leu Ala Gln Cys Asp Gly Ser Gly Asn Ile Asn Val Ser Lys Phe
    370                 375                 380

Gly Thr Asn Val Ala Gly Cys Gly Gly Phe Pro Asn Ile Ser Gln Gln
385                 390                 395                 400

Thr Pro Asn Val Tyr Phe Cys Gly Thr Phe Thr Ala Gly Gly Leu Lys
                405                 410                 415

Ile Ala Val Glu Asp Gly Lys Val Lys Ile Leu Gln Glu Gly Lys Ala
            420                 425                 430

Lys Lys Phe Ile Lys Ala Val Asp Gln Ile Thr Phe Asn Gly Ser Tyr
        435                 440                 445

Ala Ala Arg Asn Gly Lys His Val Leu Tyr Ile Thr Glu Arg Cys Val
    450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495

Ile Asp Asn Pro Lys Leu Met Asp Ala Arg Leu Phe Gln Asp Gly Pro
            500                 505                 510

Met Gly Leu Lys Lys
        515

<210> SEQ ID NO 5
<211> LENGTH: 1563
<212> TYPE: DNA
<213> ORGANISM: Staphylococcus aureus
<220> FEATURE:
<221> NAME/KEY: CDS
<222> LOCATION: (1)..(1563)

<400> SEQUENCE: 5 ttg aaa caa atc aca tgg cac gac tta caa cat atc att aaa gat ggt      48
Leu Lys Gln Ile Thr Trp His Asp Leu Gln His Ile Ile Lys Asp Gly
1               5                   10                  15 gat gtg att ggt tta cca gca tta gct gta gcc aac tta ccc gcc gaa      96
Asp Val Ile Gly Leu Pro Ala Leu Ala Val Ala Asn Leu Pro Ala Glu
            20                  25                  30 gtt cta cgt gct gtg tta gcg caa cat gac aca tat cat acg ccc aaa     144
Val Leu Arg Ala Val Leu Ala Gln His Asp Thr Tyr His Thr Pro Lys
        35                  40                  45 gat tta acg ttt ata tta gcg aat gat atc cat agt tta ggt gcc gca     192
Asp Leu Thr Phe Ile Leu Ala Asn Asp Ile His Ser Leu Gly Ala Ala
    50                  55                  60 ccg gat tta gat gat ttt ata gaa cgt cgc atg att aaa cgt gtc att     240
Pro Asp Leu Asp Asp Phe Ile Glu Arg Arg Met Ile Lys Arg Val Ile
65                  70                  75                  80 atg agc att tta acg gct tct tcc aaa acg gca caa gca atg aaa aat     288
Met Ser Ile Leu Thr Ala Ser Ser Lys Thr Ala Gln Ala Met Lys Asn
                85                  90                  95
```

```
aat gac att gaa gct tat ttt tta cca caa ggt atc att gca act cat      336
Asn Asp Ile Glu Ala Tyr Phe Leu Pro Gln Gly Ile Ile Ala Thr His
            100                 105                 110 tat cgt cag agt aat caa tta tta cct gga gtt att act aaa atc gga      384
Tyr Arg Gln Ser Asn Gln Leu Leu Pro Gly Val Ile Thr Lys Ile Gly
        115                 120                 125 tta aac aca gct gtt gat cct aga tac ggt ggc ggt aaa gta aat aca      432
Leu Asn Thr Ala Val Asp Pro Arg Tyr Gly Gly Gly Lys Val Asn Thr
    130                 135                 140 cga aca act gat gat tta gtt tca tta gta acc atc aac gat gaa aca      480
Arg Thr Thr Asp Asp Leu Val Ser Leu Val Thr Ile Asn Asp Glu Thr
145                 150                 155                 160 tac tta cat tac aca ttc cct agc gtt gat gtg gca cta ctg aga gga      528
Tyr Leu His Tyr Thr Phe Pro Ser Val Asp Val Ala Leu Leu Arg Gly
                165                 170                 175 aca tac gca gat caa caa ggt aac att tat tta act caa gaa gcg tac      576
Thr Tyr Ala Asp Gln Gln Gly Asn Ile Tyr Leu Thr Gln Glu Ala Tyr
            180                 185                 190 ttg agc gag tgt tat cat gtc gca tta aac gcg aaa gcc aat cat ggg      624
Leu Ser Glu Cys Tyr His Val Ala Leu Asn Ala Lys Ala Asn His Gly
        195                 200                 205 aaa gtt att gta caa gtt aaa gct tta gtt gat gga tat caa cta aaa      672
Lys Val Ile Val Gln Val Lys Ala Leu Val Asp Gly Tyr Gln Leu Lys
    210                 215                 220 ccg aat gaa gtt gtt atc cca gga aat ctt gtc gat tat gta tac gtc      720
Pro Asn Glu Val Val Ile Pro Gly Asn Leu Val Asp Tyr Val Tyr Val
225                 230                 235                 240 aca gaa gat gaa aag aat cac cgc caa gta att cag agt cat tat tta      768
Thr Glu Asp Glu Lys Asn His Arg Gln Val Ile Gln Ser His Tyr Leu
                245                 250                 255 cca gcc ttg tct gga gaa gaa cga att gat gga ata cct gaa ccc gca      816
Pro Ala Leu Ser Gly Glu Glu Arg Ile Asp Gly Ile Pro Glu Pro Ala
            260                 265                 270 tta cct ttt aat agt cgc aaa ttg att ctc cga cgt gct gct cag ttt      864
Leu Pro Phe Asn Ser Arg Lys Leu Ile Leu Arg Arg Ala Ala Gln Phe
        275                 280                 285 tta act tat ggc gat aca att agc atc ggt tat ggc atc aat aat gaa      912
Leu Thr Tyr Gly Asp Thr Ile Ser Ile Gly Tyr Gly Ile Asn Asn Glu
    290                 295                 300 ctc tct aat tta ttg cac gaa gaa tgt gtt gaa cat gat gtg caa ccg      960
Leu Ser Asn Leu Leu His Glu Glu Cys Val Glu His Asp Val Gln Pro
305                 310                 315                 320 att tta gat gtt ggc att ttc ggt gga ttc gtt ggg agt cgt gaa cat     1008
Ile Leu Asp Val Gly Ile Phe Gly Gly Phe Val Gly Ser Arg Glu His
                325                 330                 335 ttt ggt atg aat tac aat gca gat gtg cgc atg cct cat gat cga gca     1056
Phe Gly Met Asn Tyr Asn Ala Asp Val Arg Met Pro His Asp Arg Ala
            340                 345                 350 tgg gat ttt att tat aac aat ggt gta tca gtt gcc tat ctt agc ttt     1104
Trp Asp Phe Ile Tyr Asn Asn Gly Val Ser Val Ala Tyr Leu Ser Phe
        355                 360                 365 gct gag gtt gat caa tac ggc aat gtc aac gtg tct tac ttc aat gac     1152
Ala Glu Val Asp Gln Tyr Gly Asn Val Asn Val Ser Tyr Phe Asn Asp
    370                 375                 380 cga cta aat gga tgt ggt ggc ttt ata gac att acg caa tct gta aat     1200
Arg Leu Asn Gly Cys Gly Gly Phe Ile Asp Ile Thr Gln Ser Val Asn
385                 390                 395                 400 aaa att atc ttt tca ggt act ttt gta gct ggc agt cat gtc tca tgc     1248
Lys Ile Ile Phe Ser Gly Thr Phe Val Ala Gly Ser His Val Ser Cys
                405                 410                 415
```

```
cat aat caa cga tta aac att gaa act gaa gga caa aac cag aaa ttt       1296
His Asn Gln Arg Leu Asn Ile Glu Thr Glu Gly Gln Asn Gln Lys Phe
            420                 425                 430 gta tca gat gtg agc cat atc gac ttt aat gca caa tat tca caa tca       1344
Val Ser Asp Val Ser His Ile Asp Phe Asn Ala Gln Tyr Ser Gln Ser
        435                 440                 445 ctc gag caa gaa gtc tat ttt gtt act gag cgt gca gta ttc gaa ctc       1392
Leu Glu Gln Glu Val Tyr Phe Val Thr Glu Arg Ala Val Phe Glu Leu
    450                 455                 460 acc aat caa ggc ttg aaa cta att gaa att gca cca ggt ctt gat ttg       1440
Thr Asn Gln Gly Leu Lys Leu Ile Glu Ile Ala Pro Gly Leu Asp Leu
465                 470                 475                 480 cat aaa gat att ttg aat caa atg gct ttt aaa cca att att gct gat       1488
His Lys Asp Ile Leu Asn Gln Met Ala Phe Lys Pro Ile Ile Ala Asp
                485                 490                 495 cat tta aaa tta att gat acc agc att tac aaa gaa aaa tgg gga caa       1536
His Leu Lys Leu Ile Asp Thr Ser Ile Tyr Lys Glu Lys Trp Gly Gln
            500                 505                 510 ctt aaa caa tca att cat aaa gta tga                                   1563
Leu Lys Gln Ser Ile His Lys Val
        515                 520

<210> SEQ ID NO 6
<211> LENGTH: 520
<212> TYPE: PRT
<213> ORGANISM: Staphylococcus aureus

<400> SEQUENCE: 6

Leu Lys Gln Ile Thr Trp His Asp Leu Gln His Ile Ile Lys Asp Gly
1               5                   10                  15

Asp Val Ile Gly Leu Pro Ala Leu Ala Val Ala Asn Leu Pro Ala Glu
            20                  25                  30

Val Leu Arg Ala Val Leu Ala Gln His Asp Thr Tyr His Thr Pro Lys
        35                  40                  45

Asp Leu Thr Phe Ile Leu Ala Asn Asp Ile His Ser Leu Gly Ala Ala
    50                  55                  60

Pro Asp Leu Asp Asp Phe Ile Glu Arg Arg Met Ile Lys Arg Val Ile
65                  70                  75                  80

Met Ser Ile Leu Thr Ala Ser Ser Lys Thr Ala Gln Ala Met Lys Asn
                85                  90                  95

Asn Asp Ile Glu Ala Tyr Phe Leu Pro Gln Gly Ile Ile Ala Thr His
            100                 105                 110

Tyr Arg Gln Ser Asn Gln Leu Leu Pro Gly Val Ile Thr Lys Ile Gly
        115                 120                 125

Leu Asn Thr Ala Val Asp Pro Arg Tyr Gly Gly Lys Val Asn Thr
    130                 135                 140

Arg Thr Thr Asp Asp Leu Val Ser Leu Val Thr Ile Asn Asp Glu Thr
145                 150                 155                 160

Tyr Leu His Tyr Thr Phe Pro Ser Val Asp Val Ala Leu Leu Arg Gly
                165                 170                 175

Thr Tyr Ala Asp Gln Gln Gly Asn Ile Tyr Leu Thr Gln Glu Ala Tyr
            180                 185                 190

Leu Ser Glu Cys Tyr His Val Ala Leu Asn Ala Lys Ala Asn His Gly
        195                 200                 205

Lys Val Ile Val Gln Val Lys Ala Leu Val Asp Gly Tyr Gln Leu Lys
    210                 215                 220
```

```
Pro Asn Glu Val Val Ile Pro Gly Asn Leu Val Asp Tyr Val Tyr Val
225                 230                 235                 240

Thr Glu Asp Glu Lys Asn His Arg Gln Val Ile Gln Ser His Tyr Leu
            245                 250                 255

Pro Ala Leu Ser Gly Glu Glu Arg Ile Asp Gly Ile Pro Glu Pro Ala
            260                 265                 270

Leu Pro Phe Asn Ser Arg Lys Leu Ile Leu Arg Arg Ala Ala Gln Phe
        275                 280                 285

Leu Thr Tyr Gly Asp Thr Ile Ser Ile Gly Tyr Gly Ile Asn Asn Glu
        290                 295                 300

Leu Ser Asn Leu Leu His Glu Glu Cys Val Glu His Asp Val Gln Pro
305                 310                 315                 320

Ile Leu Asp Val Gly Ile Phe Gly Gly Phe Val Gly Ser Arg Glu His
                325                 330                 335

Phe Gly Met Asn Tyr Asn Ala Asp Val Arg Met Pro His Asp Arg Ala
                340                 345                 350

Trp Asp Phe Ile Tyr Asn Asn Gly Val Ser Val Ala Tyr Leu Ser Phe
        355                 360                 365

Ala Glu Val Asp Gln Tyr Gly Asn Val Asn Val Ser Tyr Phe Asn Asp
        370                 375                 380

Arg Leu Asn Gly Cys Gly Gly Phe Ile Asp Ile Thr Gln Ser Val Asn
385                 390                 395                 400

Lys Ile Ile Phe Ser Gly Thr Phe Val Ala Gly Ser His Val Ser Cys
                405                 410                 415

His Asn Gln Arg Leu Asn Ile Glu Thr Glu Gly Gln Asn Gln Lys Phe
            420                 425                 430

Val Ser Asp Val Ser His Ile Asp Phe Asn Ala Gln Tyr Ser Gln Ser
        435                 440                 445

Leu Glu Gln Glu Val Tyr Phe Val Thr Glu Arg Ala Val Phe Glu Leu
        450                 455                 460

Thr Asn Gln Gly Leu Lys Leu Ile Glu Ile Ala Pro Gly Leu Asp Leu
465                 470                 475                 480

His Lys Asp Ile Leu Asn Gln Met Ala Phe Lys Pro Ile Ile Ala Asp
                485                 490                 495

His Leu Lys Leu Ile Asp Thr Ser Ile Tyr Lys Glu Lys Trp Gly Gln
            500                 505                 510

Leu Lys Gln Ser Ile His Lys Val
        515                 520

<210> SEQ ID NO 7
<211> LENGTH: 23
<212> TYPE: DNA
<213> ORGANISM: Artificial Sequence
<220> FEATURE:
<223> OTHER INFORMATION: Synthetic DNA

<400> SEQUENCE: 7
atgagaaaag tagaaatcat tac                                    23

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
```
ttattttttc agtcccatgg gaccgtcctg        30

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
catttccagg agtcgttgtg        20

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
ttgtgcgtaa atccattccc        20

<210> SEQ ID NO 11
<211> LENGTH: 65
<212> TYPE: DNA
<213> ORGANISM: Artificial Sequence
<220> FEATURE:
<223> OTHER INFORMATION: Synthetic DNA

<400> SEQUENCE: 11
ccggttcgaa tctagaaata attttgttta actttaagaa ggagatatac atatgtggat        60
ggcta        65

<210> SEQ ID NO 12
<211> LENGTH: 41
<212> TYPE: DNA
<213> ORGANISM: Artificial Sequence
<220> FEATURE:
<223> OTHER INFORMATION: Synthetic DNA

<400> SEQUENCE: 12
gaaccaggcg gaacctgcag agatccaacc tatgctgagc g        41

<210> SEQ ID NO 13
<211> LENGTH: 65
<212> TYPE: DNA
<213> ORGANISM: Artificial Sequence
<220> FEATURE:
<223> OTHER INFORMATION: Synthetic DNA

<400> SEQUENCE: 13
ccggttcgaa tctagaaata attttgttta actttaagaa ggagatatac atatgtggat        60
ggcta        65

<210> SEQ ID NO 14
<211> LENGTH: 41
<212> TYPE: DNA
<213> ORGANISM: Artificial Sequence
<220> FEATURE:
<223> OTHER INFORMATION: Synthetic DNA

<400> SEQUENCE: 14
gaaccaggcg gaacctgcag agatccaacc tatgctgagc g        41

```
<210> SEQ ID NO 15
<211> LENGTH: 17
<212> TYPE: DNA
<213> ORGANISM: Artificial Sequence
<220> FEATURE:
<223> OTHER INFORMATION: Synthetic DNA

<400> SEQUENCE: 15
gtttaacttt aagaagg                                                    17

<210> SEQ ID NO 16
<211> LENGTH: 17
<212> TYPE: DNA
<213> ORGANISM: Artificial Sequence
<220> FEATURE:
<223> OTHER INFORMATION: Synthetic DNA

<400> SEQUENCE: 16
cacctacgtc aatcgct                                                    17

<210> SEQ ID NO 17
<211> LENGTH: 17
<212> TYPE: DNA
<213> ORGANISM: Artificial Sequence
<220> FEATURE:
<223> OTHER INFORMATION: Synthetic DNA

<400> SEQUENCE: 17
accaggcgga acctgca                                                    17

<210> SEQ ID NO 18
<211> LENGTH: 17
<212> TYPE: DNA
<213> ORGANISM: Artificial Sequence
<220> FEATURE:
<223> OTHER INFORMATION: Synthetic DNA

<400> SEQUENCE: 18
atccaagtgc caggagg                                                    17
```